United States Patent [19]
Davidson

[11] Patent Number: 5,405,394
[45] Date of Patent: Apr. 11, 1995

[54] DUAL COMPOSITION COUPLER FOR MODULAR MEDICAL IMPLANTS

[75] Inventor: James A. Davidson, Germantown, Tenn.

[73] Assignee: Smith & Nephew Richards, Inc., Memphis, Tenn.

[21] Appl. No.: 79,208

[22] Filed: Jun. 17, 1993

Related U.S. Application Data

[63] Continuation of Ser. No. 856,443, Mar. 24, 1992, abandoned.

[51] Int. Cl.$^6$ .............................................. A61F 2/30
[52] U.S. Cl. ........................................ 623/18; 623/16; 623/22; 623/23; 623/20
[58] Field of Search ...................... 623/16, 18, 19, 20, 623/22, 23

[56] References Cited

U.S. PATENT DOCUMENTS

| | | | |
|---|---|---|---|
| 3,707,006 | 12/1972 | Bokros et al. | 623/22 |
| 4,032,994 | 7/1977 | Frey | 623/22 |
| 4,058,856 | 11/1987 | Doerre et al. | 623/22 |
| 4,227,265 | 10/1980 | Frey | 623/22 |
| 4,687,488 | 8/1987 | Frey | 623/22 |
| 4,921,500 | 5/1990 | Averill et al. | 623/22 |
| 4,950,298 | 8/1990 | Gustilo et al. | 623/22 |
| 5,047,058 | 9/1991 | Roberts et al. | 623/20 |
| 5,080,679 | 1/1992 | Pratt et al. | 623/22 |

FOREIGN PATENT DOCUMENTS

| | | | |
|---|---|---|---|
| 0011665 | 11/1978 | European Pat. Off. | 623/22 |
| 0011665 | 6/1980 | European Pat. Off. | 623/22 |
| 0144209 | 6/1985 | European Pat. Off. | 623/22 |
| 0193681 | 9/1986 | European Pat. Off. | 623/22 |
| 0202141 | 11/1986 | European Pat. Off. | 623/22 |
| 0385572 | 9/1990 | European Pat. Off. | 623/22 |
| 2105998 | 4/1972 | France | 623/22 |
| 2310120 | 5/1975 | France | 623/22 |
| 2310120 | 12/1976 | France | 623/23 |
| 3907530 | 7/1990 | Germany | 623/23 |
| 2230192 | 10/1990 | United Kingdom | 623/22 |

OTHER PUBLICATIONS

Derwert Abstract of EPO 0 011 665 (in English) "Ceramic Endoprosthesis Hip Knee Joint Taper Sleeve Join Shank Neck Length Adjust" by Mittelmeie, H et al.; Jun. 11 1980.

Derwert Abstract of French 2 310 120 (in English) "Aluminum Ball Couple Insert Joint Metal Oxide Prosthesis Shaft Socket Titanium" by Ceraver, SA; Jan. 7 1977.

*Primary Examiner*—David Isabella
*Attorney, Agent, or Firm*—Pravel Hewitt Kimball & Krieger

[57] ABSTRACT

The invention provides an interpositional coupler for inserting between modules of a modular medical implant, wherein the modules are fabricated of compositions having different electrochemical potentials, to reduce or prevent the flow of a galvanic current and thereby reducing or preventing this contribution to corrosion of the prosthesis. The coupler may be of an insulative type comprising a zirconium/zirconium alloy core coated with blue-black zirconium oxide or nitride or any metal coated with amorphous diamond-like carbon. Alternatively, the coupler may be of a dual composition type with each of the compositions having essentially the same electrochemical potential as the module to which it couples.

8 Claims, 2 Drawing Sheets

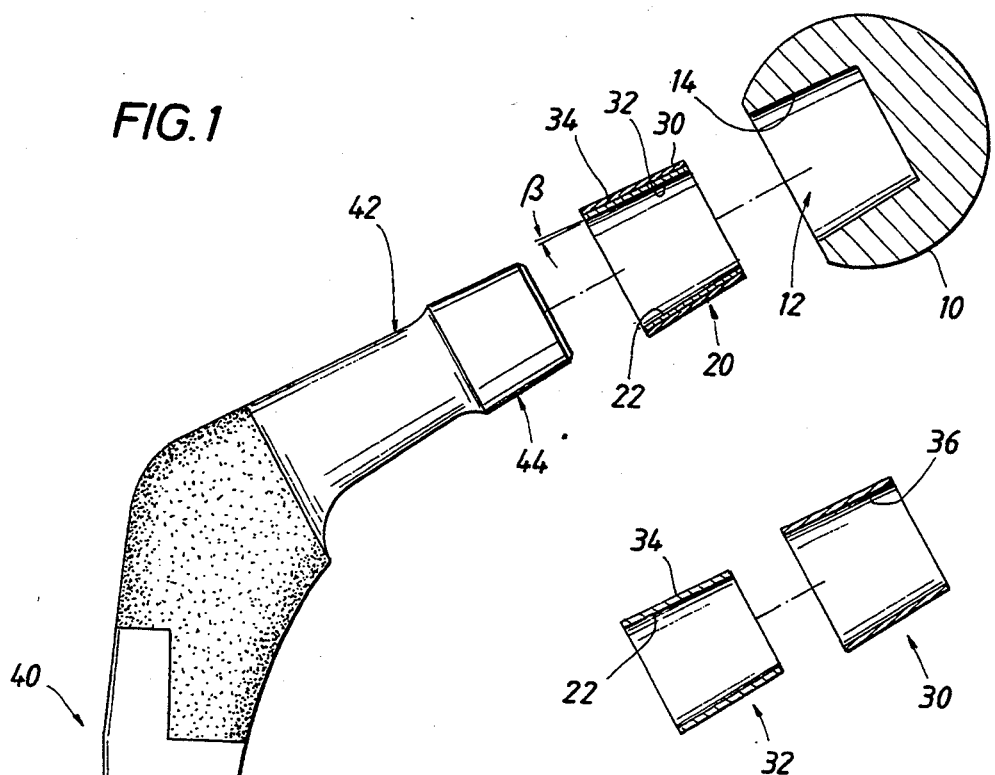
FIG. 1
FIG. 1B
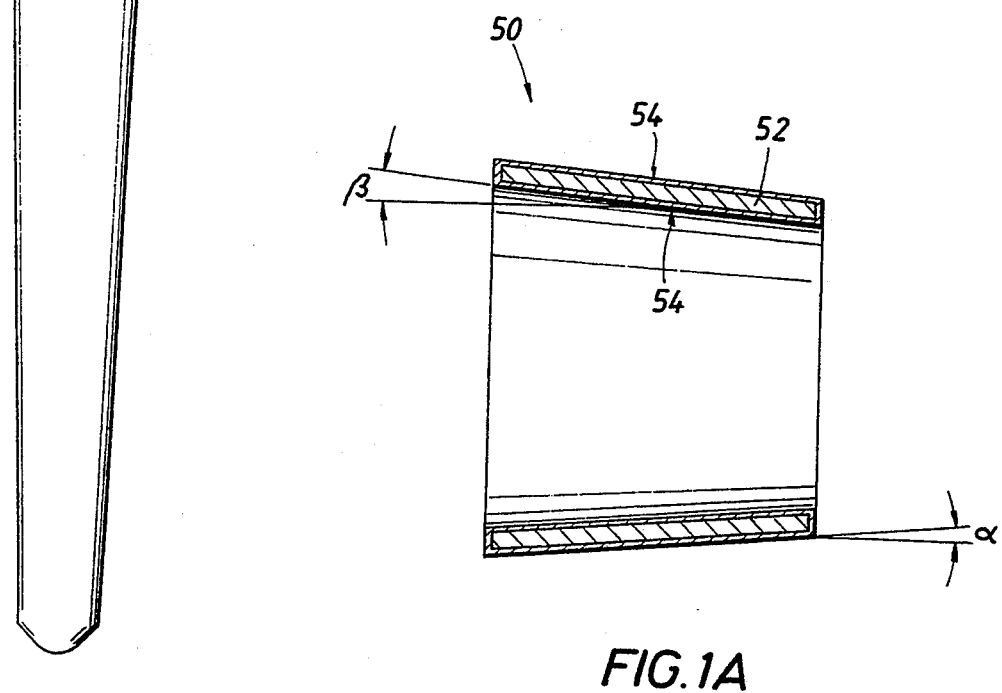
FIG. 1A

DUAL COMPOSITION COUPLER FOR MODULAR MEDICAL IMPLANTS

This is a continuation of application Ser. No. 07/856,443, filed on Mar. 24, 1992, now abandoned.

BACKGROUND

1. Field of the Invention

This invention relates to modular medical implants and more specifically to multi-component prosthetic implants where interconnecting components are made of different metallic alloys and ceramics. More specifically, the invention provides a dual composition sleeve or interpositional device which, when interposed between components of a medical prosthesis, reduces or eliminates electrochemical activity and resultant galvanic corrosion that may occur between the two modular components in the body.

2. Description of the Related Art

An increasing number of hip replacement prostheses are now based on modular designs. Typically, in such a design, the femoral head is a separate component that is press-fitted and locked onto the neck portion of the hip stem. The heads may be of inert alumina or zirconia ceramic but the most popular heads are those fabricated from a cobalt, stainless steel, or titanium alloy. Commonly, for non-cemented cases, the hip stem is made of the more flexible titanium alloys and the femoral head is made of a more abrasion resistant alloy such as a cobalt alloy. It is believed that this system gives the best long-term (non-cemented) performance. However, it has now been found that when such dissimilar alloys are used to form modules of the hip prosthesis then galvanic corrosion may contribute to dissolution of metal at the metal interface. The body fluids act as an electrolyte for the conduction of electrons and an associated low amperage current which results in electro-chemical corrosion of the alloys which may loosen the connection, and release metal ions into the body tissue.

In order to overcome this contribution of metal ions from galvanic corrosion in such modular press-fit connections, one might substitute a ceramic femoral head for the abrasion resistant cobalt alloy femoral heads. However, such a substitution, while solving the potential problem of galvanic corrosion, presents a potential new problem associated with relatively brittle ceramics: catastrophic failure of the ceramic head. For instance, U.S. Pat. No. 4,921,500 points out that when ceramic materials are used in a femoral head component, they are more "frangible" than metals and it has been found that the standard taper connections, such as the Brown and Sharpe taper, establishes hoop stresses within the ceramic femoral. When these hoop stresses exceed the strength of the ceramic material in tension, the solid ceramic head may fail with catastrophic results. To overcome this stress problem, the '500 patent discloses as its invention an adaptor fabricated of biocompatible alloy, such as titanium, having specified inner and outer taper for interposing between the borehole in the femoral head and the post on the neck of the femoral stem component. Such an adaptor is said to enable the securement of the ceramic femoral head to the post of conventional metallic femoral stems, providing a secure fit without the generation of excessive hoop stresses which could damage the ceramic femoral head.

The use of hard metallic femoral heads is however still preferred because of their resistance to damage caused by impact, greater ease of fabrication, and lower modulus of elasticity as compared to ceramics.

U.K GB 2 230 192 shows a coupler for a prosthesis having a neck made of a first material and having a first taper, and a head made of a second material with a blind bore of a second taper. The coupler has an outer surface with a taper corresponding to the second taper for co-operating with the borehole and an inner surface with a taper corresponding to the first taper for cooperating with the neck. The outer surface texture of the coupler has a first degree of coarseness for tight coupling with the inner surface of the borehole in the femoral head component. Further, the inner surface of the coupler has a surface texture of a second degree of coarseness, different from the first degree of coarseness, for tight coupling with the outer surface of the neck of the femoral stem. In the preferred embodiment, the interpositional coupler is fabricated of a titanium alloy, Ti-6Al-4V. The patent does not anywhere address the problem of galvanic corrosion when two components of a prosthesis, each having a different metallic composition than the other, are joined together in the patient's body. Indeed, this problem has only recently come to light. It is now known that after 40 months of implantation galvanic assisted corrosion occurs in 100 percent of the cases where a cobalt alloy femoral head is coupled to a Ti-6Al-4V hip stem. Although contribution from galvanic corrosion may be small for these metal combinations using proper design, it is yet desirable to reduce galvanic effects further. When the same material is used for both stem and head, no galvanic pitting corrosion is found. However, most surgeons prefer to use a harder, more abrasion resistant, metal alloy, such as the cobalt alloys, for the femoral head and a more ductile alloy, Ti-6Al-4V, for the hip stem.

What is yet needed is a method for the elimination of galvanic assisted corrosion that may occur in the body when a first component of a prosthesis having a first metal alloy composition is fixedly or removably attached to a second component of a prosthesis having a second, different metal alloy composition.

SUMMARY OF THE INVENTION

The invention provides interpositional couplers for interposing between two modules of a modular medical implant prosthesis that have different electrochemical potentials thereby preventing or reducing the flow of a galvanic current from one module to the other through the body fluid as an electrolyte and thereby eliminating or reducing galvanic assisted corrosion.

In one embodiment the invention provides a dual composition coupler or sleeve for interposing between the neck of a femoral stem component and the borehole of a metallic femoral head component to reduce or eliminate potential galvanic corrosion. The sleeve is fabricated of two metallic alloys. The first alloy is disposed on the outer surface while the second alloy is disposed on the inner surface. The outer surface alloy is the same as, or has the same electrochemical potential as, the alloy of the femoral head component while the inner surface alloy is identical to or has the same electrochemical potential as the alloy that constitutes the femoral stem component. The dual composition coupler in effect comprises two metallic sleeves nested and bonded together coextensively so that no gap exists between their nesting surfaces for an electrolyte and no galvanic current passes between the two nested sleeves of the dual composition sleeve. Consequently, when the dual composition coupler is in place, galvanic assisted corrosion in the press-fit interface of either the dual composition coupler or the femoral head and femoral stem are eliminated.

To fabricate the dual composition coupler, a metallic bond may be accomplished by friction welding, high temperature diffusion bonding, brazing, or using other processes which will eliminate the possibility of a body fluid electrolyte interposing between the two surfaces of the nested sleeves thereby preventing a potential galvanic condition which leads to corrosion.

In an alternative embodiment, a biocompatible metallic sleeve with an abrasion resistant inert, biocompatible, ceramic coating such as an oxide, nitride, or amorphous diamond-like carbon coating could also be used to electrically insulate the femoral stem from the head. Preferably, these nitride or oxide coatings are prepared in situ and have a thickness of not greater than about 5 microns. Such coatings are hard, tightly adherent to the underlying substrate and resistant to microfretting wear. It is theorized that such ceramic coated sleeves are effective because the dense ceramic surface layer acts as an insulator between the underlying metal and metal modular part fitting against the inside and outside diameter of the sleeve, so that little or no electron exchange can take place. Thus, galvanic-related effects are eliminated.

Similar dual composition couplers could also be incorporated into other modular prostheses or trauma products. For instance, these couplers could be used in the form of sleeves between bone plate holes and bone screw surfaces, or over post or extension pieces on modular hip and knee components or in the form of rectangular wedges of finite thickness between surfaces of modular components in contact with or in close proximity to other portions of such devices, such as knee joint modules. Also, couplers in the form of modular wedges may be used to alter the shape and fit of an implant. The same dual composition or insulator coupler concepts may also be applied to other non-orthopedic medical implants such as between metal components in cardiovascular, dental, or otology implants.

BRIEF DESCRIPTION OF THE DRAWINGS

The drawings show certain specific embodiments of the invention but are not intended to be limiting of the invention. Further, the drawings are schematic and representational and are not to scale.

FIG. 1 is a schematic representation of a modular hip joint with an interpositional coupler.

FIG. 1A is a schematic of an insulative coated coupler in partial cross-section.

FIG. 1B is a schematic of a two piece sleeve interpositional coupler in partial cross-section.

DETAILED DESCRIPTION OF THE PREFERRED EMBODIMENTS

Figure 2:
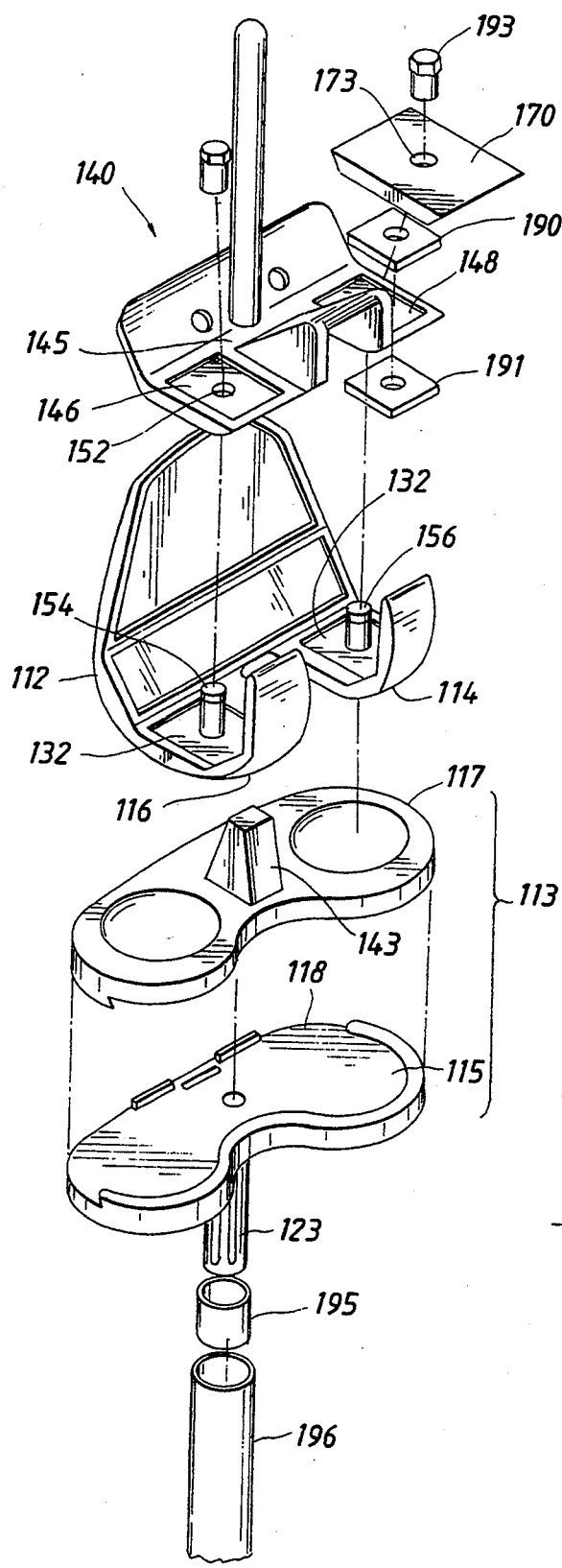
FIG. 2 is a schematic representation of a modular knee joint.

The invention provides an interposition coupler for use with modular prosthetic trauma, or other medical implants wherein the components are fabricated from different compositions with different electrochemical potentials. For example, one module of Co-Cr-Mo alloy and another of Ti-6Al-4V or 316L stainless steel; or cold-worked 316L stainless steel (such as a bone screw) used with a hot-worked or less severe cold-worked 316L stainless steel (such as a bone plate). The invention interpositional coupler provides either a direct electrical connection or an insulative layer between the modules of differing electrochemical potentials so that an electrical current cannot flow from one module to the other through the body fluids, which act as an electrolyte, and thereby inhibits potential galvanic action.

In one embodiment, a dual composition coupler comprises an outer sleeve portion having an outer surface comprising a first metallic alloy that has an electrochemical potential that is substantially identical to the electrochemical potential of a metallic alloy of a first modular prosthesis part against which the first surface is designed to fit. Generally, this means that in practice they have the same metal alloy composition. Further, the dual composition coupler has an inner sleeve portion comprising a second metallic alloy, different from the first alloy in electrochemical potential, and designed to cooperate or couple to a second prosthesis module of the same alloy composition as the inner sleeve. The outer surface of the inner sleeve portion is co-extensive with and nested tightly against the inner surface of the outer sleeve portion. Thus, electrolyte solutions are precluded from entering between the inner and outer sleeve portions so that galvanic current and potential galvanic corrosion is effectively prevented in this region.

In a second embodiment, an insulative coated sleeve is interposed between components of a modular prosthesis, trauma product, or other medical implant. This insulative sleeve or separator comprises a metal substrate with an outer surface comprising a ceramic that forms a barrier to electron exchange between two prosthesis modules. Thus, when the ceramic coated coupler fits over, for instance a screw, in a bone plate assembly, then it insulates the screw from the bone plate. These insulative couplers may be fabricated from any suitable metal for implants coated with a titanium nitride or other metal nitride or an amorphous diamond-like carbon coating. Alternatively, they may be fabricated from zirconium or its alloys coated with an in situ formed coating of blue-black zirconium oxide or zirconium nitride. The coating process is described in our U.S. Pat. No. 5,037,048, hereby fully incorporated by reference. With regard to knee joints, a modular knee joint prosthesis is disclosed in U.S. Pat. No. 4,950,298 to Gustilo et al., commonly assigned, which is fully incorporated by reference. Further, U.S. Pat. No. 5,047,058, also commonly owned and hereby fully incorporated by reference, shows inserts for the tibial component of a knee prosthesis. Neither of these patents describe a dual composition coupler designed to minimize or reduce galvanic corrosion effects.

In an example of the first embodiment, the present invention provides a dual composition coupler or sleeve for interposing between the neck of a prosthetic femoral stem component and the borehole of metallic femoral head component to reduce or eliminate potentially adverse effects from galvanic corrosion. For example, FIG. 1 shows the components of a modular hip joint prosthesis which conventionally includes a femoral head 10 and a hip joint stem body 40. The invention now adds an additional component, a dual composition sleeve 20 that is interposed between the neck and femoral head as shown in FIG. 1. The dual composition sleeve 20 is composed of two nested thin sleeves. Sleeve 32 will nest into sleeve 30, as shown in FIG. 1B, so that the outer surface 34 of sleeve 32 nests in and is coextensive with the inner surface 36 of sleeve 30. These two sleeves are then bonded together by any conventional metallic bonding process such as friction welding, high temperature diffusion bonding, brazing, and the like to eliminate any gaps between surfaces 34 and 36 which may be invaded by body fluids that act as electrolytes.

In the conventional modular hip joint prosthesis, the femoral head 10 is fabricated of a hard metallic alloy, preferably a cobalt chrome alloy, that is resistant to wear. The femoral head 10 has a borehole 12 with an inner surface 14 tapered at an angle e. The conventional non-cemented hip joint stem, preferably fabricated from Ti-6Al-4V, has a body 40 supplied with a neck 42. The proximal end of the neck 44 is tapered at an angle $\beta$. The interpositional dual composition sleeve of the invention 20 has an outer surface 34 tapered at an angle of about e for cooperating with the borehole 12 in the femoral head. Further, the dual composition sleeve 20 has an inner surface 22 tapered at an angle of about $\beta$ for cooperating with the outer surface of the tapered proximal end of the neck portion 44. Thus, when assembled, the dual composition sleeve fits tightly into the femoral head and tightly over the proximal end of the neck thereby mechanically coupling the hip joint stem 40 to the femoral head 10.

When the invention modular hip joint prosthesis described above is implanted into a patient, the presence of the dual composition sleeve prevents potential galvanic corrosion within the interface between the femoral head and the hip joint stem by providing similar metals at the head-sleeve and stem neck-sleeve contact points.

As an alternative, the interpositional insulative sleeve 50 shown in FIG. 1A may be used. This sleeve is fabricated from zirconium or a zirconium alloy core 52 the surfaces 54 of which has been coated with blue-black or black zirconium oxide or zirconium nitride to a depth of about 5 microns or less. This sleeve insulates the head from the stem thereby preventing potential galvanic action. As a further alternative, the interpositional sleeve may be fabricated from any suitable metal coated with a ceramic such as an oxide or nitride or an amorphous diamond-like carbon coating.

From FIG. 2, the essential modular components of a knee joint prosthesis include a primary femoral component 112, which cooperates with a tibial component 113. The femoral component 112 is a generally J-shaped member and includes a pair of laterally spaced apart femoral condyle portions 114 and 116, each of which is smoothly, convexly curved in lateral profile similar to the curvature of the anatomical femoral condyle. The tibial component 113 comprises a tibial base portion 115 for accommodating and affixing a tibial platform 117 thereon. The tibial base portion 115 includes a floor portion 118 configured to resemble the overall configuration of the upper end portion of the tibia which is prepared to receive the base portion. The base portion 115 includes a stabilizing post 123 extending from its inferior surface and insertable into the tibial medullary canal to provide for stabilizing the component on the tibia. This post 123 may also have an extension portion which is fit tightly onto the post. An invention sleeve 195 may also be used to galvanically isolate the tibial post 123 from the extension post 196, as shown in FIG. 2. Platform 117 is shaped generally in the configuration of base portion 115, and is designed to fit onto platform 115. Further, a centrally located stabilizer post 143 may be positioned on the upper face of tibial platform 117 for knee stability if the posterior cruciate ligament is removed. When a stabilizer post is used, the femoral component must be modified to engage this post and provide stability.

To accommodate a modular adapter component, the femoral modular platform 140 includes a base portion 145 joined to a pair of spaced apart platform portions 146 and 148. Each of the base portions include a bore 152 for receiving pin members 154 and 156 which are mounted on condyle portions 114 and 116 and extend upwardly from surfaces 132. These pin members 154 and 156 are aligned with bores 152 to enable platform 140 to be secured to primary femoral component 112. One of the modular components may include a rectangular plate 170 which is positioned as seen in FIG. 2 on the face portions 146 and 148 of platform 170. These plates 170 include a bore 173 for allowing pin members 156 and 154 to be secured therethrough. As can be readily seen, it may be desirable to fabricate femoral component 112 from a different metallic alloy than platform 140. Furthermore, rectangular modular plates 170 may be fabricated from yet a different metallic alloy. Finally, the tibial platform 115 may also be fabricated by a different metallic alloy. Usually, the receiving tibial platform 117 is fabricated from ultra-high molecular weight polyethylene.

For the modular attachment of femoral knee components, dual compositional inserts may be interposed between the interfaces of any of these components. For example, inserts 190 and 191 may be used to galvanically separate the module 140 and nut 193, and the module 140 or femoral component 112, respectively. These dual-composition components may have one side of a metal essentially matching the composition of the metal it mates with (e.g., Ti alloy femoral module) and the other side of a metal essentially matching the composition of the metal of the counter-mating component (e.g., Co-Cr-Mo femoral component). Alternatively, the dual compositional sleeve or separator may be a metal substrate which has an inert, dense oxide or nitride ceramic surface layer or amorphous diamond-like carbon surface layer.

Figure 3:
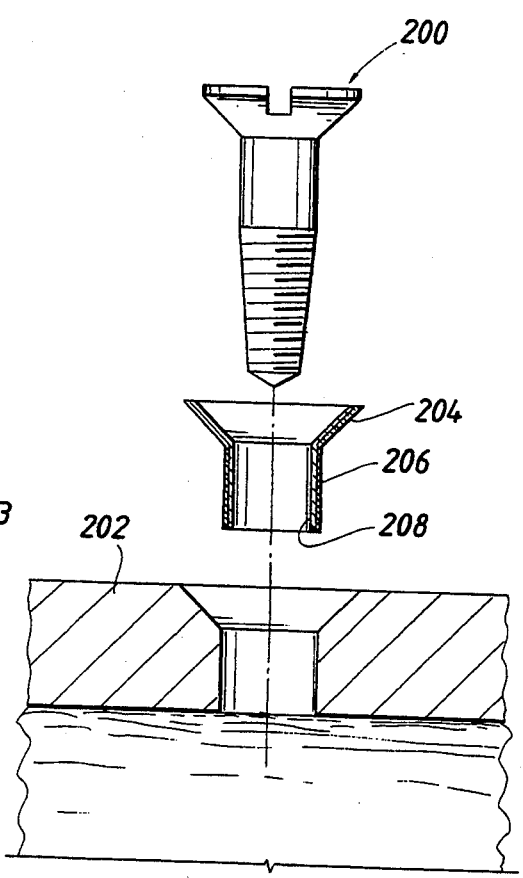
FIG. 3 is a schematic representation of a bone screw and bone plate with an interpositional coupler.

Further, screws may be used to anchor the tibial base plate to the bone by inserting through counter-sunk bore holes in the tibial base plate beneath the tibial platform 117. This assembly is similar in cross section to that shown in FIG. 3 for the bone plate and bone screw trauma implant. Thus, a screw module 200 is driven through bone plate module 202 and holds the bone plate in place. An interpositional coupler 204 is interposed between the screw 200 and plate 202. This coupler 204 comprises an outside sleeve surface 206 the same as the metal of the plate 202 and an inner metal sleeve 208 the same as the metal of the screw 200. Alternatively, the screw 200 or bone plate 202 or both may be fabricated from zirconium or a zirconium alloy and maybe coated with a blue-black or black zirconium oxide or zirconium nitride coating. As a further alternative, either the screw or the bone plate or both may be coated with an oxide or nitride ceramic or an amorphous diamond-like carbon coating. This type of coupler will insulate screw from bone thereby preventing potential galvanic action.

The invention has been described with reference to its preferred embodiment. One of ordinary skill in the art, upon reading the above disclosure, may comprehend changes and modifications that are within the scope of the specification as set forth above and the claims herebelow.

I claim:

1. A dual composition sleeve for interposing between two components of a modular medical implant, the sleeve comprising:
   (a) an outer sleeve portion having an outer surface adapted for coupling with a first modular component of an implant exposed to electrolyte fluids in a body of a recipient, said outer surface comprising a first metallic alloy that has an electrochemical potential substantially identical to that of the first modular component against which the outer surface is designed to couple; and
   (b) an inner sleeve portion comprising a second metallic alloy different than the first alloy, the outer surface of said inner sleeve portion being bonded to and co-extensive with the inner surface of the outer sleeve portion so that electrolyte fluids are precluded from entering between the inner and outer sleeve portion, the second alloy having substantially the same electrochemical potential as a second modular component of the implant, said second modular component adapted to couple with an inner surface of the inner sleeve portion.

2. The sleeve of claim 1, wherein the dual composition sleeve has a frusto-conical exterior and the inner surface of the inner sleeve portion is adapted to fit over a neck of a prosthetic hip joint stem and the outer surface of the outer sleeve portion is adapted to fit within a bore in a femoral head.

3. The sleeve of claim 1, wherein the inner surface of the inner sleeve portion is adapted to cooperate with a groves of a screw and the outer surface of a outer sleeve portion is adapted to cooperate with a hole in a bone plate.

4. In combination, modules of a modular implant, comprising:
   a first module of an implant adapted for implanting in a body of a recipient where the implant is exposed to electrolyte body fluids, said module comprised of a first composition having a first electrochemical potential;
   a second module of the implant comprised of a second composition having an electrochemical potential different than the first composition; and
   an interpositional coupler module shaped to fit between a cooperating surface of the first module designed to cooperate with a cooperating surface of the second module, said coupler comprising:
   (a) a first surface, having a metallic composition identical to the composition of the first module and adapted to fit snugly against the cooperating surface of the first module; and
   (b) a second surface bonded to the first surface, the second surface having a metallic composition identical to the composition of the cooperating surface of the second module and adapted to fit snugly against the cooperating surface of the second module;
   wherein, when the coupler is inserted between the first and second modules of the body of the patient, then galvanic activity through electrolytic body fluid between the metallic compositions of the first and second modules is effectively prevented.

5. The combination of claim 4 wherein the first and second modules are cooperating modules of a modular knee prosthesis and the coupler is of a substantially rectangular wedge shape of finite thickness for interposing between the modules.

6. The combination of claim 4 wherein the modular implant is a modular knee prosthesis, the first module comprises a tibial post, the second module comprises an exterior post, and the coupler is of substantially cylindrical shape for interposing between the tibial post and the extension post.

7. The combination of claim 4 wherein the first module comprises a bone plate with a hole for receiving a screw, the second module is a bone screw for fitting into the hole for holding the bone plate in place, and the coupler is shaped to interpose between the hole in the bone plate and the screw that fits into the hole.

8. The combination of claim 4 wherein the modular implant is a modular hip implant, the first module is a hip joint stem comprising a neck, the second module is a femoral head with a bore therein, and the interpositional coupler comprises a substantially frusto-conical shaped sleeve sized for fitting over the neck of the hip joint stem and snug insertion into the bore of the femoral head.

* * * * *